United States Patent [19]

Cussler et al.

[11] Patent Number: 5,827,538
[45] Date of Patent: Oct. 27, 1998

[54] OSMOTIC DEVICES HAVING VAPOR-PERMEABLE COATINGS

[75] Inventors: Edward L. Cussler, Edina, Minn.; Scott M. Herbig, Bend, Oreg.; Kelly L. Smith, Bend, Oreg.; Paul van Eikeren, Bend, Oreg.

[73] Assignee: Pfizer Inc., New York, N.Y.

[21] Appl. No.: 571,980

[22] PCT Filed: May 19, 1994

[86] PCT No.: PCT/IB94/00114

§ 371 Date: Jan. 17, 1996

§ 102(e) Date: Jan. 17, 1996

[87] PCT Pub. No.: WO95/03033

PCT Pub. Date: Feb. 2, 1995

Related U.S. Application Data

[63] Continuation of Ser. No. 96,144, Jul. 22, 1993, abandoned.
[51] Int. Cl.$^6$ .................................................. A61K 9/24
[52] U.S. Cl. ........................ 424/473; 424/451; 424/464; 424/489; 604/892.1
[58] Field of Search .................................. 424/473, 451, 424/464, 489; 604/892.1

[56] References Cited

U.S. PATENT DOCUMENTS 3,832,252  8/1974  Higuchi ............................... 424/424 X

FOREIGN PATENT DOCUMENTS 2166052  4/1986  United Kingdom ............. A61K 9/00
93/06819  4/1993  WIPO ............................. A61K 9/00

Primary Examiner—D. Gabrielle Phelan
Attorney, Agent, or Firm—Peter C. Richardson; Gregg C. Benson; A. Dean Olson

[57] ABSTRACT

An osmotic device that, following the imbibement of water vapor, provides for the controlled release of a beneficial agent to an aqueous environment. The device comprises a hydrophilic formulation including a beneficial agent, and if needed, an osmagent, surrounded by a wall. The wall is formed at least in part of a semipermeable hydrophobic membrane having an average pore size between about 0.1 $\mu$m and 30 $\mu$m. The pores are substantially filled with a gas phase. The hydrophobic membrane is permeable to water in the vapor phase and the hydrophobic membrane is impermeable to an aqueous medium at a pressure less than about 100 Pa. The beneficial agent is released, for example, by osmotic pumping or osmotic bursting upon imbibement of sufficient water vapor into the device core. These devices minimize incompatibilities between the beneficial agent and ions (such as hydrogen or hydroxyl) or other dissolved or suspended materials in the aqueous medium, since contact between the beneficial agent and the aqueous medium does not occur until after the beneficial agent is released. This results from the semipermeable membrane's selective permeability for water vapor. In addition, the high water fluxes attendant with these vapor-permeable membranes facilitate the delivery of beneficial agents having low solubilities, and the delivery of high dosages of beneficial agents.

28 Claims, 5 Drawing Sheets

5,827,538

OSMOTIC DEVICES HAVING VAPOR-PERMEABLE COATINGS

This application was filed under 35 U.S.C. §371 based on PCT/IB94/00114, which was filed on May 19, 1994 which is a continuation of U.S. application Ser. No. 08/096,144 which was filed on Jul. 22, 1993 and is now abandoned.

BACKGROUND OF THE INVENTION

Osmotic delivery systems based on semipermeable coatings have been described in the literature (e.g., Baker, R. W., "Controlled Release of Biologically Active Agents", pp.132–133, 1987; Smith, K. L. and Herbig, S. M., "Controlled Release" in Membrane Handbook, Ho, W. S. W., and Sirkar, K. K., eds., pp. 915–935, 1992) and produced commercially for several years. Osmotic delivery systems have been developed that release the beneficial agent either in a sustained manner or as a bolus (osmotic bursting systems; e.g., U.S. Pat. Nos. 3,247,066, 3,952,741, B1 4,016,880 and 4,177,256). These delivery systems rely on semipermeable coatings to allow influx of water and to contain the beneficial agent within the core until it is released.

Generally, semipermeable coatings are either dense, microporous, or asymmetric in structure (e.g., U.S. Pat. Nos. 3,845,770, 4,968,507, and European Patent Application 89308716.3, Publication No. 0357369). In addition, typically the semipermeable membranes must be wetted by an aqueous solution to allow for release of the beneficial agent (Batt, B. C., "An Experimental Study of Osmotic Pumping by Highly Microporous Polymer Membranes," M.S. thesis, University of Kansas, 1982; U.S. Pat. Nos. 4,0851,228 and 4,340,054). Also, a delivery port(s) must be formed in thesemipermeable coating (e.g.,by drilling a hole(s), or by forming pores in the coatings) for sustained delivery of a beneficial agent. Alternatively, the beneficial agent can be released by bursting the coating as a result of hydrostatic pressure generated in the core by osmosis.

Osmotic devices have been described that have a combination of a hydrophilic semipermeable membrane covering a portion of the device and a hydrophobic porous membrane covering another portion of the device. The devices contain hydrophobic liquids (e.g., oils) which inherently wet the hydrophobic membrane (i.e., are entrained in the membrane pores; the pores are typically less than 100 $\mu$). Water is imbibed through the hydrophilic semipermeable membrane into the device and the resultant hydrostatic pressure forces the oils out through the hydrophobic membrane pores. Thus, these devices facilitate the osmotic delivery of oils or beneficial agents dissolved in oils. Such devices are described in Merfeld, A. E., Haslam, J. L. and Rork, G. S., "An In Vitro Release Method for Lipoidal Materials", Inter. Journal of Pharm., Vol. 69, No.1, pp.63–67, 1991; U.S. Pat. No. 4,685,918; and International Application WO 92/05775.

In contrast to osmotic devices, diffusional release of beneficial agents through pores in hydrophobic "nonsemipermeable" coatings has also been described in the literature (e.g., Junginger, H. E., and J. Verhoven, "Controlled Release of Drugs with Microporous Polymers", Proceedings of 11th International symposium on Controlled Release of Bioactive Materials, Controlled Release Society, Lincolnshire, Ill., pp.4–5, 1984; Kruisbrink, J., and G. J. Boer, Journal of Pharm. Sci., Vol.73, No. 12, pp. 1713–1718, Dec. 1984; and U.S. Pats. Nos. 4,871,542, 4,756,844, 4,002,458). Generally these coatings have large pores (e.g., >100 $\mu$). In general, the beneficial agent (or solution containing beneficial agent) must wet the pores of the coating. The large pores facilitate wetting of the pores by an aqueous beneficial-agent-containing solution. Thus, the microporous membranes control the release of beneficial agent by controlling the surface area available for diffusion into the environment of use.

One particular device is described in commonly assigned U.S. patent application Ser. No. 07/982,815 entitled "Supported Liquid Membrane Delivery Devices" the disclosure of which is hereby incorporated by reference. This application discloses supported liquid membrane delivery devices that release a beneficial agent to an aqueous environment following exposure to an environmental trigger. A microporous hydrophobic support membrane surrounds a beneficial agent-containing hydrophilic formulation. A hydrophobic liquid is held within the microporous support membrane by capillarity and the hydrophobic liquid is substantially impermeable to the aqueous environment and the beneficial agent-containing hydrophilic formulation. The entrained hydrophobic liquid becomes substantially permeable to the aqueous environment upon exposure to an environmental trigger, such as an enzyme, and the beneficial agent is subsequently released by either diffusion or osmotic pumping.

In another field of art, the field of chemical separation, hydrophobic microporous membranes are commonly available and are used in gas-transport/liquid-barrier applications. They have been used to selectively transport vapors and act as barriers to liquids. Examples of such use are blood oxygenators, membrane distillation processes, and breathable waterproof fabrics. Vapor permeable coatings have also been used as selective and/or protective coatings on sensors or sorbents. Sensor devices used to detect gases are commonly coated with a hydrophobic microporous film to prevent the electrode from becoming wetted. In addition, ion-exchange resins have been coated with vapor permeable coatings for the selective removal of ammonia. Methods to make vapor permeable membranes and their application are described in several references (e.g., Synthetic Polymer Membranes, R. E. Kesting, 1985).

Although the above-described devices make a significant advance in the field of delivery devices there is a continuing search for alternative delivery devices.

SUMMARY OF INVENTION

This invention is directed to an osmotic device that, following the imbibement of water vapor, provides for the controlled release of a beneficial agent to an aqueous environment. The device comprises a hydrophilic formulation including a beneficial agent, and if needed, an osmagent, surrounded by a wall. The wall is formed at least in part of a semipermeable hydrophobic membrane having an average pore size between about 0.1 $\mu$m and 30 $\mu$m. The pores are substantially filled with a gas phase. The hydrophobic membrane is permeable to water in the vapor phase and the hydrophobic membrane is impermeable to an aqueous medium at a pressure less than about 100 Pa. The beneficial agent is released, for example, by osmotic pumping or osmotic bursting upon imbibement of sufficient water vapor into the device core.

These devices minimize incompatibilities between the beneficial agent and ions (such as hydrogen or hydroxyl) or other dissolved or suspended materials in the aqueous medium, since contact between the beneficial agent and the aqueous medium does not occur until after the beneficial agent is released. This results from the semipermeable membrane's selective permeability for water vapor. In addition, the high water fluxes attendant with these vapor-permeable membranes facilitate the delivery of beneficial agents having low solubilities, and the delivery of high dosages of beneficial agents.

Other objects, features and advantages of the invention will be more apparent to those skilled in the art from the following detailed specification, taken in conjunction with the figures and the accompanying claims.

DETAILED DESCRIPTION OF THE INVENTION

Figure 1:
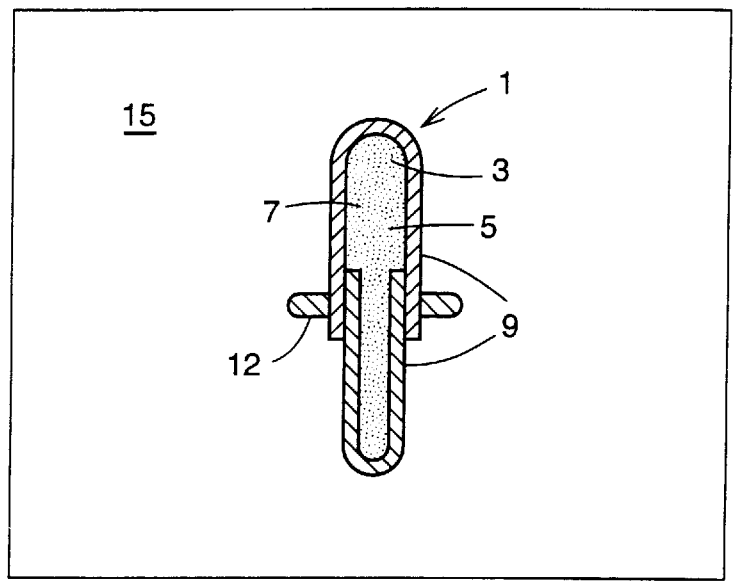
FIG. 1 is a cross-sectional view of an exemplary capsule of this invention.

Typically, in the devices of this invention water vapor is imbibed into the core from the environment of use through the pores in the membrane due to osmosis (liquid water is repelled by the hydrophobicity of the membrane; liquid water will not wet the pores of the membrane). Due to water vapor imbibition, a hydrostatic pressure is developed within the core. The hydrostatic pressure in the core can cause the hydrophilic formulation in the core to wet the largest pores in the coating and thus allow beneficial agent to be released (thus the hydrostatic pressure overcomes the hydrophobicity i.e., surface tension, of the hydrophobic membrane) in a sustained manner by an osmotic pumping mechanism. Alternatively, for example, the hydrostatic pressure can cause the vapor-permeable semipermeable membrane to burst, releasing the beneficial agent as a bolus.

Any semipermeable hydrophobic membrane (membrane means) that is solid under the conditions of use, is permeable to water vapor, and the pores of which are substantially filled with a gas phase and are not wetted by the aqueous medium in the environment of use, may be used in this invention. By aqueous medium is meant a composition containing water as the principal liquid component (e.g., physiological fluids, solutions of organic or inorganic substances particularly electrolytes and mixtures of substances in water, moist soil). By substantially filled with a gas phase is meant that most of the pores do not contain solids or liquids that block the pores, but contain gases such as oxygen, nitrogen or water vapor. Typically the hydrophobic membrane has pores having an average pore size between about 0.1 $\mu$m and 30 $\mu$m, preferably less than 10 $\mu$m, and the hydrophobic membrane is impermeable to water at a pressure less than about 100 Pa.

Preferably, the hydrophobic membrane has a water vapor transmission rate greater than 2 g-mm/m$^2$-24 hour, a contact angle with water greater than 50 degrees, and a total pore volume of between 5% and 95%. Preferably, the membrane material itself (in the nonporous state) is substantially impermeable to the beneficial agent or beneficial-agent-containing formulation (i.e., the beneficial agent will not diffuse through the membrane material to an appreciable extent). By impermeable is meant less than 1% of the agent or formulation is released through the membrane material over a 24 hour period. In addition, preferably the membrane material (in the nonporous state) has an intrinsic permeability to water of less than 1×10$^{-6}$ cc (STP)-cm/cm$^2$-sec-cmHg. Although the membrane thickness may be any dimension that provides structural stability, the membrane is preferably 5 $\mu$m to 5 mm in thickness. Preferably the membrane is 10 $\mu$m to 1 mm for human applications. Preferably, for osmotic bursting devices the semipermeable membrane material has a combination of thickness and material strength so that once the desired hydrostatic pressure has been generated (due to diffusion of water vapor into the device) within the core, the membrane is disrupted thus releasing the beneficial agent. The pores in the membrane must create at least one continuous pathway through the membrane thickness. Although typically the membrane surrounds the beneficial agent, the membrane may be combined with another type of semipermeable or impermeable wall portion to totally surround the beneficial agent, if desired. Preferably, the semipermeable hydrophobic membrane surrounds about 20% to about 100% of the device surface. Preferably the membrane is polymeric or a wax, although appropriately treated inorganic materials such as ceramics, metals, or glasses may be used.

The following is a preferred listing of materials that can be used to make the vapor-permeable membrane of this invention. The polymer's molecular weight should be of such a size that the polymer is solid at the temperature of use and appropriate for the application (e.g., pharmaceutically acceptable or EPA approved).

Cellulose esters such as cellulose acetate, cellulose acetate acetoacetate, cellulose acetate benzoate, cellulose acetate butylsulfonate, cellulose acetate butyrate, cellulose acetate butyrate sulfate, cellulose acetate butyrate valerate, cellulose acetate caprate, cellulose acetate caproate, cellulose acetate caprylate, cellulose acetate carboxymethoxypropionate, cellulose acetate chloroacetate, cellulose acetate dimethaminoacetate, cellulose acetate dimethylaminoacetate, cellulose acetate dimethylsulfamate, cellulose acetate dipalmitate, cellulose acetate dipropylsulfamate, cellulose acetate ethoxyacetate, cellulose acetate ethyl carbamate, cellulose acetate ethyl carbonate, cellulose acetate ethyl oxalate, cellulose acetate furoate, cellulose acetate heptanoate, cellulose acetate heptylate, cellulose acetate isobutyrate, cellulose acetate laurate, cellulose acetate methacrylate, cellulose acetate methoxyacetate, cellulose acetate methylcarbamate, cellulose acetate methylsulfonate, cellulose acetate myristate, cellulose acetate octanoate, cellulose acetate palmitate, cellulose acetate propionate, cellulose acetate propionate sulfate, cellulose acetate propionate valerate, cellulose acetate p-toluene sulfonate, cellulose acetate succinate, cellulose acetate sulfate, cellulose acetate tripropionate, cellulose acetate valerate, cellulose benzoate, cellulose butyrate napthylate, cellulose butyrate, cellulose chlorobenzoate, cellulose cyanoacetates, cellulose dicaprylate, cellulose dioctanoate, cellulose dipentanate, cellulose dipentanlate, cellulose formate, cellulose methacrylates, cellulose methoxybenzoate; cellulose nitrate, cellulose nitrobenzoate, cellulose phosphate (sodium salt), cellulose phosphinates, cellulose phosphites, cellulose phosphonates, cellulose propionate, cellulose propionate crotonate, cellulose propionate isobutyrate, cellulose propionate succinate, cellulose stearate, cellulose sulfate (sodium salt), cellulose triacetate, cellulose tricaprylate, cellulose triformate, cellulose triheptanoate, cellulose triheptylate, cellulose trilaurate, cellulose trimyristate, cellulose trinitrate, cellulose trioctanoate, cellulose tripalmitate, cellulose tripropionate, cellulose trisuccinate, cellulose trivalerate, cellulose valerate palmitate.

Cellulose ethers such as ethyl cellulose, ethyl cellulose sulfate, or ethylcellulose dimethylsulfamate.

Polysulfones.

Polyethersulfones.

Polycarbonates.

Polyurethanes.

Polyvinyl acetates.

Polyamides.

Polysiloxanes.

Polyesters.

Polyalkenes such as polyethylene, ethylene vinyl alcohol copolymer, polypropylene, poly(1,2-dimethyl-1-butenylene), poly(1-bromo-1-butenylene), poly(1, butene), poly(1-chloro-1-butenylene),poly(1-decyl-1-butenylene), poly(1-hexane),poly(1-isopropyl-1-butenylene), poly(1-pentene), poly(3-vinylpyrene), poly(4-methoxy-1-butenylene); poly(ethylene-co-methyl styrene), poly vinylchloride, poly(ethylene-co-tetrafluoroethylene), poly(ethylene-terephthalate), poly(dodecafluorobutoxylethylene), poly(hexafluoroprolylene), poly(hexyloxyethylene), poly(isobutene), poly(isobutene-co-isoprene), poly(isoprene), poly-butadiene, poly[(pentafluoroethyl)ethylene], poly[2-ethylhexyloxy)ethylene], poly(butylethylene), poly(tertbutylethylene), poly(cylclohexylethylene), poly[(cyclohexylmethyl)ethylene], poly(cyclopentylethylene), poly(decylethylene), poly(dodecylethylene), poly(neopentylethylene), poly(propylethylene).

Polystyrenes such as poly(2,4-dimethyl styrene), poly(3-methyl styrene), poly(4-methoxystyrene), poly(4-methoxystyrene-stat-styrene), poly(4-methyl styrene), poly(isopentyl styrene), poly(isopropyl styrene).

Polyvinyl esters or polyvinyl ethers such as poly(benzoylethylene), poly(butoxyethylene), poly(chloroprene), poly(cyclohexioxyethylene), poly(decyloxyethylene), poly(dichloroethylene), poly(difluoroethylene), poly(vinyl acetate), poly(vinyltrimethyilstyrene).

Polyacrylic acid derivatives such as polyacrylates, polymethyl methacrylate, poly(acrylic acid) higher alkyl esters, poly(ethylmethacrylate), poly(hexadecyl methacrylate-co-methylmethacrylate), poly(methylacrylate-co-styrene), poly(n-butyl methacrylate), poly(n-butyl-acrylate), poly(cyclododecyl acrylate), poly(benzyl acrylate), poly(butylacrylate), poly(secbutylacrylate), poly(hexyl acrylate), poly(octyl acrylate), poly(decyl acrylate), poly(dodecyl acrylate), poly(2-methyl butyl acrylate), poly(adamantyl methacrylate), poly(benzyl methacrylate), poly(butyl methacrylate), poly(2-ethylhexyl methacrylate), poly(octyl methacrylate), acrylic resins.

Polyethers such as poly(octyloxyethylene), poly(oxyphenylethylene), poly(oxypropylene), poly(pentyloxyethylene), poly(phenoxy styrene), poly(secbutroxylethylene), poly(tert-butoxyethylene).

Exemplary membrane natural and synthetic waxes include: insect and animal waxes such as chinese insect wax, beeswax, spermaceti, fats and wool wax; vegetable waxes such as bamboo leaf wax, candelilla wax, carnauba wax, Japan wax, ouricury wax, Jojoba wax, bayberry wax, Douglas-Fir wax, cotton wax, cranberry wax, cape berry wax, rice-bran wax, castor wax, indian corn wax, hydrogenated vegetable oils (e.g., castor, palm, cottonseed, soybean), sorghum grain wax, Spanish moss wax, sugarcane wax, caranda wax, bleached wax, Esparto wax, flax wax, Madagascar wax, orange peel wax, shellac wax, sisal hemp wax and rice wax; mineral waxes such as Montan wax, peat waxes, petroleum wax, petroleum ceresin, ozokerite wax, microcrystalline wax and paraffins; and synthetic waxes such as polyethylene wax, Fischer-Tropsch wax, chemically modified hydrocarbon waxes and cetyl esters wax.

Especially preferred membrane materials include polyethylene, polyvinylidene fluoride, polyacrylic acid derivatives, cellulosic derivatives such as cellulose esters and natural or synthetic waxes.

The semipermeable membrane surrounds at least part of the device core. The device core contains the beneficial agent. If the beneficial agent is not an osmagent then the core must also contain an osmagent. The osmagent may be any material that increases the osmotic pressure of the core such that the osmotic pressure of the core is greater than that of the surrounding environment of use. A higher osmotic pressure within the core allows the hydrostatic pressure in the core to increase to achieve either the desired osmotic pumping or the desired membrane disruption (bursting). The core must have an effective osmotic pressure greater than that of the surrounding aqueous medium in the environment of use (e.g., 700 KPa in humans) so that there is a net driving force for water vapor to enter the core. The osmagent can be either soluble or swellable. Examples of osmotically effective solutes are inorganic and organic salts and sugars. Osmotically effective compounds may be used singly or in combination and include magnesium sulfate, magnesium chloride, sodium chloride, lithium chloride, potassium sulfate, sodium carbonate, sodium sulfite, lithium sulfate, potassium chloride, calcium carbonate, sodium sulfate, calcium sulfate, potassium acid phosphate, calcium lactate, d-mannitol, urea, inositol, magnesium succinate, tartaric acid, water soluble acids, alcohols, surfactants, and carbohydrates such as sugars (e.g., raffinose, sucrose, glucose, lactose, fructose), sugar derivatives, algin, sodium alginate, potassium alginate, carrageenan, fucoridan, furcellaran, laminaran, hypnea, gum arabic, gum ghatti, gum karaya, locust bean gum, pectin and starch. For the devices of this invention which are to be employed to deliver a drug to humans or animals, any such solute should be pharmaceutically acceptable. A preferred device comprising such a solute contains a range of 15 to 95% osmotically effective solute (e.g., osmagent or beneficial agent that is an osmagent).

Typically for those devices that function by osmotic bursting (e.g., capsules sealed with an adhesive material) a water-swellable component such as a hydrogel is used. The swellable excipient aids in forcing the capsule cap off of the capsule body, or in bursting the coating, as a result of the imbibement of water vapor into the device core. For analogous reasons swellable components can be added to tablets and beads. Exemplary hydrogels include polyacrylic acid derivatives (e.g., polyacrylates, poly-methyl methacrylate, poly(acrylic acid) higher alkyl esters, poly (ethylmethacrylate), poly(hexadecyl methacrylate-co-methylmethacrylate), poly(methylacrylate-co-styrene), poly (n-butyl methacrylate), poly(n-butyl-acrylate), poly (cyclododecyl acrylate), poly(benzyl acrylate), poly (butylacrylate), poly(secbutylacrylate), poly(hexyl acrylate), poly(octyl acrylate), poly(decyl acrylate), poly(dodecyl acrylate), poly(2-methyl butyl acrylate), poly(adamantyl methacrylate), poly(benzyl methacrylate), poly(butyl methacrylate), poly(2-ethylhexyl methacrylate), poly(octyl methacrylate), acrylic resins), polyacrylamides, poly (hydroxy ethyl methacrylate), poly(vinyl alcohol), poly (ethylene oxide), poly N-vinyl-2-pyrrolidone, naturally occurring resins such as polysaccharides (e.g., dextrans, water-soluble gums, starches, chemically modified starches), cellulose derivatives (e.g., cellulose esters, cellulose ethers, chemically modified cellulose, microcrystalline cellulose, sodium carboxymethylcellulose and methylcellulose).

Preferred hydrogels include ethylene oxide derivatives such as polyethylene oxide (PEO) because of its relatively large capacity to absorb water and swell, its availability in a variety of different molecular weights in commercial quantities, its biocompatibility, and its safety and favorable toxicity properties. PEO is commercially available and can be obtained having a variety of different molecular weights. Other preferred hydrogels are starches, gums, crosslinked hydrogels, and carboxymethylcellulose.

The hydrogel employed can be a blend of, for example, two or more polymers. For example, different hydrogels comprising blends of PEO polymers of different molecular weights can be prepared and employed. Such blends can be adjusted to assist in achieving the desired delivery rates for the beneficial agents.

In particular the excipients may include a surfactant such as sodium lauryl sulfate, lecithin, polyethylene glycol, sorbitan esters, polyoxyethylene sorbitan esters, polyvinylpyrrolidone, polyoxyethylene oil derivatives, polyglycolized glycerides, propylene glycol esters, glycerides, and polyoxamers. The surfactants lower the surface tension within the core and aid in wetting the pores once sufficient hydrostatic pressure is reached in the core.

The beneficial agents used in the devices of this invention include for example, any physiologically or pharmacologically active substance that produces a localized or systemic effect in animals including mammals (e.g., human beings).

Preferably the beneficial agents are hydrophilic, or are contained in a hydrophilic formulation. By hydrophilic is meant that it will not diffuse through, or, not have high solubility in the hydrophobic semipermeable membrane material (in the nonporous state). Alternatively, by hydrophilic is meant that the formulation has no more than a certain diffusive flux through the gas-filled membrane. For example, if less than 10% of the total agent is released by diffusion in 3 hours from a tablet with a 100 mg drug load, a 3 cm$^2$ surface area, and 100 $\mu$m-thick coating, then a maximum flux of beneficial agent/hydrophilic formulation is 0.01 mg-cm/cm$^2$hr. This inhibits premature leaking of the beneficial agent through the hydrophobic membrane into the environment of use.

Examples of active substances include inorganic and organic compounds such as drugs that act on the peripheral nerves, adrenergic receptors, cholinergic receptors, nervous system, skeletal muscles, cardiovascular smooth muscles, blood circulatory system, synaptic sites, neuroeffector junctional sites, endocrine and hormone systems, immunological system, reproductive system, autacoid systems, alimentary and excretory systems, inhibitors of autocoids, and histamine systems. The pharmaceutical agent that can be delivered for acting on these systems includes anti-depressants, hypnotics, sedatives, psychic energizers, tranquilizers, anti-convulsants, muscle relaxants, antisecretories, anti-parkinson agents, analgesics, anti-inflammatory agents, local anesthetics, muscle contractants, antibiotics, anti-microbials, anthelmintics, anti-malarials, hormonal agents, contraceptives, histamines, antihistamines, adrenergic agents, diuretics, antiscabiotics, anti-pediculars, anti-parasites, anti-neoplastic agents, hypoglycemics, electrolytes, vitamins, diagnostic agents and cardiovascular pharmaceuticals.

Also included in such active substances are prodrugs of the above-described drugs. Such drugs or prodrugs can be in a variety of forms such as the pharmaceutically acceptable salts thereof.

The term beneficial agent is also meant to include other substances for which it is desirable and/or advantageous to control delivery into an environment of use. Examples of such substances include: agrichemicals such as insecticides, herbicides, fertilizers, fungicides, pheromones, algaecides, insect growth regulators, plant growth regulators, reaction catalysts, reaction feedstocks, pH controlling agents, enzymes, enzyme inhibitors, disinfectants, absorbants, flavors and fragrances.

In addition to the above-mentioned ingredients of the devices of this invention, other common pharmaceutical excipients may be present. Examples include viscosity modifiers, antioxidants, stabilizers, pH controlling agents, flavoring agents, binding agents, tablet disintegrants, osmotic agents, lubricants, glidants, adsorbents, inert diluents, etc. Typical examples are: binding agents such as carboxymethyl cellulose, hydroxyethyl cellulose, acacia gum, guar gum, microcrystalline cellulose, starch sodium alginate, polyethylene glycols, corn syrup, sucrose, lactose, mannitol, calcium phosphate and ethyl cellulose; tablet disintegrants such as starch, microcrystalline cellulose, clays and sodium alginate, polyethylene glycols, corn syrup, sucrose, lactose, mannitol, calcium phosphate and ethyl cellulose; tablet disintegrants such as starch, microcrystalline cellulose, clays and sodium alginate; lubricants such as talc, polyethylene glycol, corn starch, sodium benzoate and sodium acetate; glidants such as microfine silicas, corn starch, microcrystalline cellulose and talc; adsorbents such as silicas and starches; inert diluents such as lactose, dextrose, starch, microcrystalline cellulose, calcium phosphate, calcium sulfate, sucrose, mannitol, kaolin and magnesium aluminum sulfate; and osmotic agents and buffering agents such as citric acid, sodium phosphate, glucose, potassium citrate, potassium sorbate, sodium bicarbonate, sodium chloride and sodium citrate.

The release profile can be tailored so that the release duration is from instantaneous (i.e., bursting) to 24 hours and more. For example, a tablet containing a core formulation with a water-swellable hydrogel designed to expand and burst the tablet has a very short release duration, essentially as fast as the beneficial agent could dissolve. A tablet in which the beneficial agent is released by osmotic pumping or diffusion through the pores has a longer release duration. In addition, release rates can be increased by decreasing the surface tension of the capsule excipients as demonstrated in Example 14.

The release profile of the devices of this invention can also be advantageously tailored by altering time lags between exposure of the device to the environmental aqueous vapor and release of the beneficial agent. Thus, preferably the membrane pores, membrane composition and membrane thickness are of a number, composition and size sufficient to provide the desired time lag (e.g., sufficient time lag to provide drug release to the human ileum, colon, duodenum, or jejunum). Typically, for example, vapor-permeable membranes with larger pores (within the constraints given above) become wetted with water from the core faster than similar membranes with smaller pores. In addition, thinner or more-porous membranes typically burst faster and/or allow for quicker osmotic pumping than thicker or less-porous membranes. Thus, for example, preferably a one-to-ten-hour time lag is sufficient to provide release to the duodenum, ileum, jejunum or colon if the device begins imbibing water vapor immediately after ingestion.

Preferred devices include those described in Examples 1,9 and 14 and described generally below. Particularly preferred devices include those having a semipermeable membrane of polyethylene or polyvinylidene fluoride surrounding the beneficial agent. Capsule type devices may be sealed together with an adhesive such as cellulose acetate. It is especially preferred that the hydrophilic formulation contains an osmagent that is a sugar or sugar derivative such as meglumine. Particularly preferred is when the hydrophilic formulation has a surface tension of about 60–75 dyn/cm. In another preferred device the hydrophilic formulation contains meglumine and polyethylene glycol and the hydrophilic formulation has a surface tension of about 40–60 dyn/cm. In another preferred device the hydrophilic formulation contains meglumine and sodium lauryl sulfate and the hydrophilic formulation has a surface tension of about 25–40 dyn/cm.

Although any mixture of the above ingredients may be used that satisfactorily delivers the beneficial agent, typically the membrane is about 1% to about 50% by weight of the device. The amount of beneficial agent is the amount that is sufficient to achieve the desired effect (e.g., therapeutic effect). Typically the amount of osmagent is about 10% to about 90% by weight of the device. The remainder weight can be made up of any desired formulation ingredients (described above) and other additives.

The devices of this invention can also be administered within a capsule comprising a water-soluble wall. For example, the devices can be manufactured to be of suitable size for inclusion either singularly or multiply within a gelatin capsule such that when the capsule dissolves the device(s) are released into the environment of use. While the devices to be included within a capsule can be of a variety of shapes, a preferred shape for such devices is spherical or substantially spherical. The exact number and size of such devices can and will be determined according to a variety of well known factors. For example, the environment of use, the beneficial agent or agents, the amount of beneficial agent and the rate of release are all factors to be considered in determining the size, shape, and number of devices to be included in such capsules as well as the composition of the capsule.

The dispensing device shape and dimensions can vary based on the particular application (e.g., tablets, beads or capsules). Common exemplary shapes are spherical, cylindrical, tablet-shape, and capsular-shape. The dispensing device dimensions may vary with the desired application (e.g., cattle tablets, human tablets). The shape and size may also vary depending on the application so that for example the tablet is suitable depending on the quantity and rate of beneficial agent delivery which vary based on the application. Preferably, for human and animal applications, the tablet is 5 to 20 mm in diameter and the beads are 0.1 to 5 mm in diameter. However, typical capsule dimensions range from about 1 cm to about 2.5 cm in length and about 0.3 cm to about 1 cm in diameter for human health applications. For animal applications, such as ruminal delivery to cattle, typical dimensions range from about 5 cm to about 10 cm in length and about 1 cm to about 3 cm in diameter. For other applications, such as agrichemicals, chemical reactions, flavors, and fragrances, shapes and sizes will be determined by the method of use and may be different from those listed above.

Figure 2:
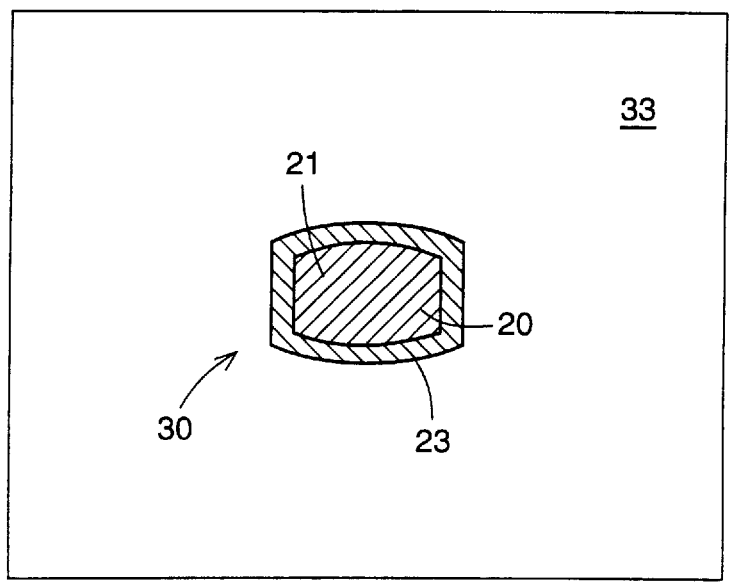
FIG. 2 is a cross-sectional view of an exemplary tablet of this invention.

A clearer understanding of the devices of this invention may be had by reference to FIGS. 1 and 2. In FIG. 1 the beneficial agent 3 and other excipients (e.g., osmagent 5, hydrogel 7) are surrounded by vapor permeable semipermeable membrane 9 capsule halves. Joining the semipermeable membrane 9 capsule halves is a band of adhesive material 12. External to the device 1 is the environment of use 15 including the aqueous medium. In FIG. 2 the beneficial agent 20 and other excipients (e.g., osmagent 21) are surrounded by a vapor-permeable semipermeable membrane 23. External to the device 30 is the environment of use 33.

The devices of this invention may be made using the above-described materials using the following processes and other conventional methods.

Microporous coatings can be made by a variety of methods, such as phase inversion, scintering, leaching, and irradiation. Several different phase-inversion methods, such as the vapor-quench process, the dry process, the liquid-quench process, and the thermal process, can be used to form microporous coatings. In addition, commercially available microporous films or microporous hollow fibers can be used in this invention.

In the vapor-quench process, membrane formation is accomplished by penetration of a precipitant for the polymer into the solution film from the vapor phase, which may be saturated With the solvent used. A porous membrane is produced without a skin and with an even distribution of pores over the membrane thickness.

In the dry process, the polymer is dissolved in a mixture of a solvent and a poor solvent, of which the solvent is more volatile. The polymer precipitates when the mixture shifts in composition during evaporation to a higher nonsolvent content. A skinned or nonskinned microporous membrane can be the result.

In the liquid-quench process, film formation is caused by the immersion of a film or coating or polymer solution into a nonsolvent bath. The polymer precipitates as a result of solvent loss and nonsolvent penetration (exchange of the solvent with nonsolvent). A skinned or nonskinned membrane can be the result.

In the thermal process, a solution of polymer in a latent solvent is brought to phase separation by a cooling step. When evaporation of the solvent is not prevented, the membrane typically will be porous.

Microporous coatings can also be made by inclusion of a leachable component in the coating formulation. For example, small particles of sugar, salt, or water-soluble materials equal to the desired pore size can be suspended or dissolved in the coating solution. Once the coating is applied, the water-soluble materials can be leached out by immersion in water, forming a microporous structure. Alternatively, the small particles can consist of volatile solids such as menthol, ammonium acetate, or ammonium carbonate.

Microporous hydrophobic films have also been made by scintering particles of hydrophobic polymers or ceramics or metals together under heat and pressure. Microporous hydrophobic films are also commonly made by irradiation. Films can be cured (precipitated) by irradiation, forming a microporous structure. In addition, pores can be formed in dense films by a nucleation track-etched method. All of these methods for forming hydrophobic microporous films have been described in the literature, especially for use as membranes for separations (*Synthetic Polymer Membranes,* by R. E. Kesting; John Wiley & Sons, 1985).

The above methods to make microporous coatings are applied in the following paragraphs to make vapor-permeable capsules and coatings on tablets and granules.

Capsules having vapor-permeable membrane capsule walls may be made according to the following description. The desired polymers can be melted in a solution with a latent solvent and then capsule mandrels can be dip-coated in this heated polymer solution (e.g., Examples 1 and 2). Upon cooling, the polymer solidifies and then the capsules can be trimmed and removed from the mandrels. This dip-coating process is essentially the same as the process to produce commonly available gelatin capsules. To make the capsules vapor permeable, an additional processing step is required to remove the latent solvent. The latent solvent can be removed by vacuum-drying the capsules, or placing the capsules in a liquid that is more volatile and miscible with the latent solvent and thus extracting the latent solvent from the capsules. The capsules are then air-dried to remove the extracting liquid. These capsules can then be filled with beneficial agent and other desired excipients by standard capsule-filling techniques. After filling, the capsule halves must be fixed in place so they do not separate prematurely during use. The capsule halves may be sealed together using an adhesive, or formed such that they snap-fit together, or crimped such that the capsule cap is fixed to the capsule body. Preferably water insoluble adhesives are used because, if the capsules comes apart prematurely, it may not function in the desired manner. For ruminal applications an impermeable wall portion may be joined between the cap and body portions.

Vapor-permeable membrane coated capsules may also be made by dip-coating mandrels into coating solutions that form microporous coatings by the dry process or by the liquid-quench process. Capsules made by the dry process require drying the coating solution on the mandrels before trimming and removing the capsules. Capsules made by the liquid-quench process require that the dip-coated mandrels be dipped/immersed into a liquid quench bath to solidify the capsules. The capsules could either be removed while wet, or dried and then removed from the mandrels.

Capsules may also be produced by forming a cap and body of sintered polymers. Typically, the desired polymers are molded into the desired porous shapes and sintered. The beneficial agent and any other ingredients are placed into the structure as a mixture or in succession. Then the capsule is assembled and joined by conventional methods used for gelatin capsules.

Tablets may be prepared using conventional processes and conventional tableting and tablet-coating equipment. Tablets may be made for example by compressing blends (using conventional tableting methods) of beneficial agent and any other additives to form a tablet core.

Granules (beads or multiparticulates) of the beneficial agent and other excipients may be made by conventional extrusion/spheronization or fluid bed granulation techniques.

Vapor permeable coatings may be applied to the above-described tablets, capsules, or granules using conventional coating equipment such as fluid bed coaters and pan coaters. Vapor permeable coatings may be applied using conventional equipment by spray-coating solutions that form microporous coatings by a phase-inversion dry or thermal process, as described above and in Examples 3 and 5. In addition, coating solutions that contain leachable components may be applied using conventional equipment and typical processes and then, once coated, the leachable component may be extracted from the coating. The leachable component may be extracted by a liquid (as described in Examples 4 and 6) or may be extracted by evaporation (e.g., vacuum drying).

Vapor permeable coatings may also be applied to tablets or capsules by a dip-coating process. Tablets or capsules may be dip-coated by immersing one-half of the tablet or capsule in the coating solution, and upon formation of a coating, immersing the other half of the tablet or capsule in the coating solution (as is done for currently marketed pharmaceuticals). Vapor permeable coatings applied by dip-coating can be formed by the thermal process, dry process, liquid quench process, or extraction of leachable components, as described above.

In addition, flat-sheet microporous films can be sealed together, forming pouches that contain beneficial agents. The flat-sheet microporous film can also be sealed over the opening of an impermeable container. Alternatively, hollow fibers having microporous walls can be used with their ends sealed, enclosing the beneficial agent within the lumen of the fiber.

Methods for using the devices of this invention include administration of the appropriate devices to animals via oral administration or by insertion of the appropriate devices into a body cavity of the animal. Devices of this invention can also be used to deliver agents to such environments of use as swimming pools, ponds, fish tanks, soil, crops and aqueous chemical and/or enzymatic reaction systems. In such cases, the devices are placed into the desired environment of use. The devices of this invention require that such environment of use be either aqueous or provide for contact of the device with water or other aqueous medium.

It should be understood that the invention is not limited to the particular embodiments shown and described herein, but that various changes and modifications may be made without departing from the spirit and scope of this novel concept as defined by the following claims.

TABLE 1

Products Used in Examples

| Product | Company | Location |
| --- | --- | --- |
| CA 398-10 cellulose acetate | Eastman Chemical Co. | Kingsport, Tennessee |
| Teflon MP 1000 polytetrafluoroethylene | DuPont Chemical Co. | Wilmington, Delaware |
| Sudan IV dye | Sigma Chemical Co. | St. Louis, Missouri |
| Coomassie Blue G-250 dye | J. T. Baker, Inc. | Phillipsburg, New Jersey |
| Kynar 460 polyvinylidene fluoride | Atochem North America, Inc. | Philadelphia, Pennsylvania |
| Kynar 761 polyvinylidene fluoride | Atochem North America, Inc. | Philadelphia, Pennsylvania |
| Kynar 711 polyvinylidene fluoride | Atochem North America, Inc. | Philadelphia, Pennsylvania |
| Kynar 461 polyvinylidene fluoride | Atochem North America, Inc. | Philadelphia, Pennsylvania |
| Kimwipe tissue | Kimberly-Clark | Roswell, Georgia |
| Fluoroglide fluoropolymer aerosol spray | Norton | Wayne, New Jersey |
| Methocel E6 hydroxypropyl methylcellulose | Dow Chemical Co. | Midland, Michigan |
| Ethocel S100 ethylcellulose | Dow Chemical Co. | Midland, Michigan |
| STREA-1 fluidized bed spray coater | Aeromatic, Inc. | Columbia, Maryland |
| Dowex MSC-1 ion | Dow Chemical Co. | Midland, Michigan |

TABLE 1-continued

Products Used in Examples

| Product | Company | Location |
|---|---|---|
| exchange beads | | |
| Avicel PH101 microcrystalline cellulose | FMC Corp. | Philadelphia, Pennsylvania |
| AcDisol sodium carboxymethyl-cellulose | FMC Corp. | Philadelphia, Pennsylvania |
| Klucel hydroxypropyl-cellulose | Aqualon | Hopewell, Virginia |
| Tenite 808A polyethylene | Eastman Chemical Co. | Kingsport, Tennessee |
| Povidone C-15 polyvinyl pyrrolidone | ISP Technologies, Inc. | Wayne, New Jersey |

EXAMPLE 1

Formation of Vapor-permeable Membrane Capsules

Capsules were made with vapor-permeable (VP) membrane walls. A polymer solution of 17 wt % Tenite 808A polyethylene and 0.085 wt % talc dissolved in olive oil at 160° C. was used to make the capsules. The solution was used immediately after preparation.

Capsules were formed by dip-coating aluminum mandrels with the polymer solution and then quenching the solution to precipitate the polymer. The mandrels were preheated in a 145° C. oil bath. The heated mandrels were dipped into the coating solution, withdrawn slowly (about 3 seconds to completely withdraw the mandrel) and then quenched 5 seconds in liquid nitrogen. They were then immersed in acetone for 30 to 40 minutes to remove the oil from the pores in the capsule walls. The capsules were then dried at room temperature. The capsules were taken off the mandrels when dry, and cut for length. The capsule cap and capsule body were sealed with a sealing solution consisting of 15 wt % CA 398-10 cellulose acetate, 28 wt % ethanol, and 0.1 wt % Coomassie Blue G-250 dye dissolved in acetone. The capsules were sealed by rotating the capsules and applying a thin stream of sealing material (from a syringe needle) around the joint between the capsule cap and body. The sealant was allowed to air dry at room temperature.

Capsules formed by the process described above had walls microporous in structure with an overall thickness of about 300 μm. The void volume of the capsule walls was about 80% and the pore size was generally less than 1 μm diameter.

EXAMPLE 2

Formation of Vapor-permeable Membrane Capsules

Capsules were made with VP membrane walls. A polymer solution of 15 wt % Kynar 460 polyvinylidene fluoride dissolved in dimethyl formamide at room temperature was used to make the capsules.

Capsules were formed by dip-coating aluminum mandrels with the polymer solution and then quenching the solution in ethanol to precipitate the polymer. The mandrels were wiped with a Kimwipe tissue that had been sprayed with Fluoroglide fluoropolymer aerosol spray lubricant. The mandrels were dipped into the coating solution and withdrawn very slowly (about 10 seconds to completely withdraw the mandrel). They were then air-dried for 7 seconds before quenching by immersion in ethanol for 40 minutes, followed by a second ethanol quench for 15 minutes. The coated mandrels were then rinsed in deionized (DI) water for 20 minutes, and allowed to dry at ambient conditions. The capsules were taken off the mandrels when dry, and cut for length.

Capsules formed by the process described above had walls microporous in structure with an overall thickness of about 130 μm. The void volume of these capsule walls was greater than 80% and the pore size was generally less than 1 μm in diameter.

EXAMPLE 3

Formation of Vapor-permeable Membrane Tablet Coatings Applied by Spray Coating

TABLE 2

Vapor-permeable coating solutions were made with the following formulations:

| Method | Polymer | Pore Formers | Solvent |
|---|---|---|---|
| #1 | 3 wt % Kynar 711 polyvinylidene fluoride | 5 wt % $H_2O$, 25 wt % Butanol | 67 wt % Acetone |
| #1 | 3 wt % Kynar 711 polyvinylidene fluoride | 9.5 wt % $H_2O$ | 87.5 wt % Acetone |
| #1 | 3 wt % Kynar 461 polyvinylidene fluoride | 35 wt % n-Propanol | 62 wt % Acetone |
| #1 | 3 wt % Kynar 461 polyvinylidene fluoride | 8 wt % $H_2O$, 15 wt % Acetic Acid | 74 wt % Acetone |
| #2 | 3 wt % Kynar 461 polyvinylidene fluoride | 15 wt % Acetic Acid | 52 wt % Acetone |

The solutions made by Method 1 were made by dissolving the Kynar polyvinylidene fluoride in one-half of the solvent at 50° to 55° C. The pore formers were dispersed in the remaining acetone and slowly added to the Kynar solution maintaining the temperature at 50° to 55° C. To get a more porous membrane structure, the Kynar and water formulation was made by an alternative procedure, Method 2. In Method 2, the Kynar and water were premixed with vigorous stirring at about 70° C. to a frothy consistency. The acetone was then added and the Kynar solution dissolved. The solutions (made by either method) were used immediately after mixing.

Pseudoephedrine tablets were made by standard direct-compression techniques. The tablets consisted of 180.00 mg pseudoephedrine HCl; 69.15 mg anhydrous lactose; 112.20 mg dicalcium phosphate, anhydrous; 40.80 mg Ethocel S100 ethycellulose; 20.40 mg Povidone C-15 polyvinyl pyrrolidone; 45.00 mg isopropanol; 45.00 mg ethanol; 25.20 mg sodium chloride; and 2.25 mg magnesium stearate, for a total weight of 450.00 mg. Isopropanol and ethanol are volatile and their weights are not included in the total weights.

The tablets were precoated by spray-coating with a solution of 5 wt % sucrose and 5 wt % Methocel E6 Premium hydroxypropyl methylcellulose dissolved in deionized water using a STREA-1 (Aeromatic) fluid-bed spray coater. The precoated tablets were then spray-coated using the STREA-1 with a Kynar solution from the formulations described above.

Equipment: STREA-1 with Plexiglass bowl for precoat and stainless steel Wurster bowl (without pipe support) for vapor-permeable coat, 1.0 mm nozzle, peristaltic pump, balance, and 90 psi house air supply.

TABLE 3

| Typical Spray Conditions | Precoat | Vapor-Permeable Coating |
|---|---|---|
| Sample size | 200 g | 200 g |
| Inlet air temperature | 100° C. | 52° C. |
| Feed solution spray rate | 10 g/min | 11 g/min |
| Atomization air pressure | 200–300 KPa | 200–300 KPa |
| Blowback air pressure | 0 Pa | 0 Pa |
| Fluidization air rate | 130 m$^3$/hr | 130 m$^3$/hr |

The coatings formed in the manner described above were porous, and the thickness was controlled by the coating time.

EXAMPLE 4

Formation of Vapor-permeable Membrane Tablet Coatings Applied by Spray-coating Followed by Extraction A VP coating solution was made of 3 wt % Kynar 711 polyvinylidene fluoride, with 5 wt % glycerol and 15 wt % n-propanol as pore formers, dissolved in acetone following the procedure described as Method 1 in Example 3. The solution was used immediately after mixing.

Pseudoephedrine tablets made by standard direct-compression techniques as described in Example 3 were precoated by spray-coating with a solution of 5 wt % sucrose and 5 wt % Methocel E6 Premium hydroxypropyl methylcellulose dissolved in deionized water using a STREA-1 (Aeromatic) fluid-bed spray-coater. The precoated tablets were then spray-coated using the STREA-1 with the Kynar polyvinylidene fluoride solution described above.

TABLE 4

Equipment: STREA-1 with Plexiglass bowl for precoat and stainless steel Wurster bowl (without pipe support) for VP coat, 1.0 mm nozzle, peristaltic pump, balance, and 90 psi house air supply.

| Typical Spray Conditions | Precoat | Vapor-Permeable Coating |
|---|---|---|
| Sample size | 200 g | 200 g |
| Inlet air temperature | 100° C. | 52° C. |
| Feed solution spray rate | 10 g/min | 0 g/min |
| Atomization air pressure | 200–300 KPa | 200–300 KPa |
| Blowback air pressure | 0 Pa | 0 Pa |
| Fluidization air rate | 130 m$^3$/hr | 130 m$^3$/hr |

The glycerol contained in the membrane tablet coating was then removed by extraction with ethanol. The coated tablets were immersed in ethanol for 10 minutes to extract the glycerol and then air-dried at ambient temperature.

EXAMPLE 5

Formation of Vapor-permeable Membrane Bead Coatings Applied by Spray-coating

TABLE 5

Vapor-permeable coating solutions were made with the following formulations:

| Polymer | Pore Formers | Solvent |
|---|---|---|
| 3 wt % Kynar 711 polyvinylidene fluoride | 5 wt % H$_2$O, 25 wt % Butanol | 67 wt % Acetone |
| 3 wt % Kynar 711 polyvinylidene fluoride | 9.5 wt % H$_2$O | 87.5 wt % Acetone |

The coating solutions were prepared as described in Example 3 (Method 2). The coating solutions were used immediately after mixing.

Dowex MSC-1 ion exchange resin beads were soaked in deionized water and then fluidized in a STREA-1 spray-coater. The beads were then coated with the solutions described above using the following conditions:

TABLE 6

Equipment: STREA-1 with stainless steel Wurster bowl for VP coat, 1.0 mm nozzle, peristaltic pump, balance, and 90 psi house air supply.

| Typical Spray Conditions | Vapor-Permeable |
|---|---|
| Sample size | 100 g |
| Inlet air temperature | 52° C. |
| Feed solution spray rate | 10 g/min |
| Atomization air pressure | 200 KPa |
| Blowback air pressure | 0 Pa |
| Fluidization air rate | 130 m$^3$/hr |

The coating formed in the manner described above was porous, and the thickness was controlled by the duration of spray coating to a thickness of 20 μm to 80 μm.

EXAMPLE 6

Formation of Vapor-permeable Membrane Bead Coatings Applied by Spray-coating Followed by Extraction A vapor-permeable coating solution was made of 3 wt % Kynar 711 polyvinylidene fluoride, with 5 wt % glycerol and 15 wt % n-propanol as pore formers, dissolved in acetone following the procedure described in Example 3 (Method 1). The solution was used immediately after mixing.

Dowex MSC-1 ion exchange resin beads were soaked in deionized water and then fluidized in a STREA-1 spray-coater. The beads were then coated with the solution described above using the following conditions:

TABLE 7

Equipment: STREA-1 with stainless steel Wurster bowl for VP coat, 1.0 mm nozzle, peristaltic pump, balance, and 90 psi house air supply.

| Typical Spray Conditions | Vapor-Permeable |
|---|---|
| Sample size | 100 g |
| Inlet air temperature | 52° C. |
| Feed solution spray rate | 10 g/min |
| Atomization air pressure | 200 KPa |
| Blowback air pressure | 0 Pa |
| Fluidization air rate | 130 m$^3$/hr |

The glycerol contained in the membrane tablet coating was then removed by extraction with ethanol. The coated beads were immersed in ethanol for 5 minutes to extract the glycerol and then were air-dried at ambient temperature.

EXAMPLE 7

Demonstration of Release of Glipizide from Vapor-permeable Membrane Capsules

Capsules were made with vapor-permeable membrane walls. A polymer solution of 17% Kynar 460 polyvinylidene fluoride, diluted and melted in propylene carbonate at 120° C., was used to make the capsules. The solution was used immediately after mixing.

Capsules were formed by dip-coating aluminum mandrels with the polymer solution and then quenching the solution to precipitate the polymer. The mandrels were prepared as described in Example 1. The mandrels were dipped into the coating solution, withdrawn slowly and then quenched in liquid nitrogen for 5 seconds. They were then put in an exchange bath of ethanol for at least 45 minutes. The capsules were allowed to dry, then were rewet with ethanol to facilitate removal from the mandrel. The capsules were cut for length. A core consisting of 10 wt % glipizide and 90 wt % meglumine for a total of 200 mg was loaded into the capsule body and the capsule was then sealed with the sealing solution described in Example 1.

Figure 3:
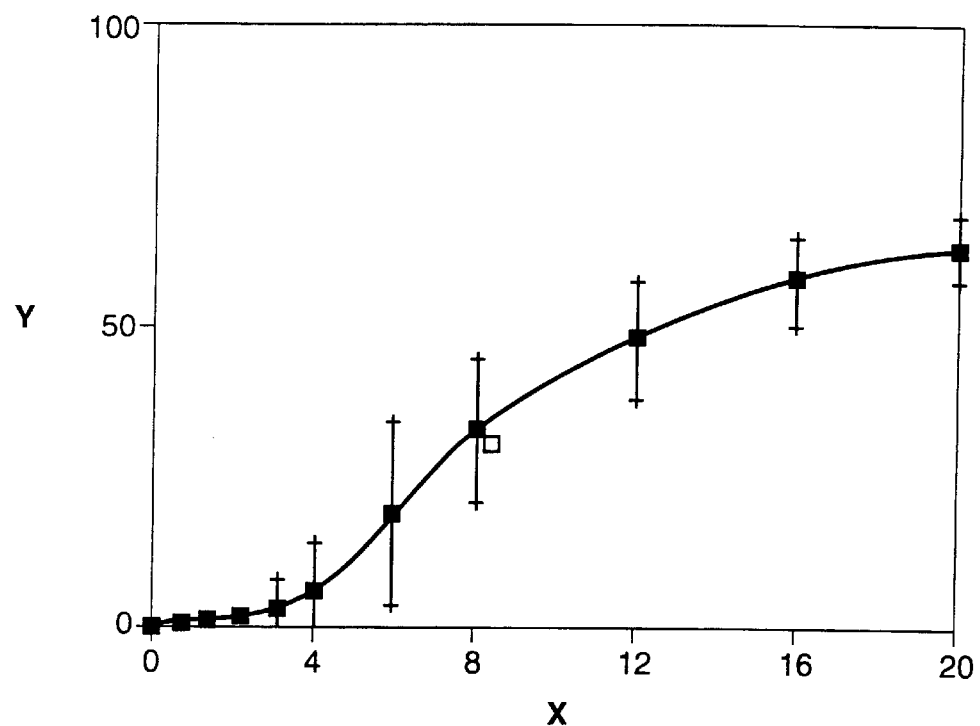
FIG. 3 is a graph showing glipizide release from vapor permeable membrane coated capsules made of porous Kynar 460 polyvinylidene fluoride.

Release-rate tests were conducted in simulated intestinal buffer (pH 7.5, containing potassium phosphate, monobasic, and sodium hydroxide with an osmotic pressure of 700 KPa at 37° C. with continuous stirring. Glipizide solubility is about 0.34 mg/ml in simulated intestinal buffer. The capsules were each placed in 1 liter simulated intestinal buffer for 24 hours. FIG. 3 shows the release of glipizide from VP membrane capsules into simulated intestinal buffer. In FIG. 3 glipizide release as a percent of total glipizide (Y) is graphed against time in hours (X).

EXAMPLE 8

Demonstration of Release of Pseudoephedrine from Vapor-permeable Membrane Coated Tablets Pseudoephedrine tablets made by standard direct-compression techniques had a total weight of 350 mg and consisted of 14 wt % pseudoephedrine, 41 wt % lactose, 40 wt % Avicel PH101 microcrystalline cellulose and 5 wt % AcDiSol sodium carboxymethylcellulose. These tablets were coated with a VP-membrane coating from a solution consisting of 3 wt % Kynar 461 polyvinylidene fluoride, 35 wt % n-propanol, and 62 wt % acetone. This coating solution was prepared as described in Example 3 (Method 1) and was applied by the same spray-coating process as described in Example 3.

Figure 4:
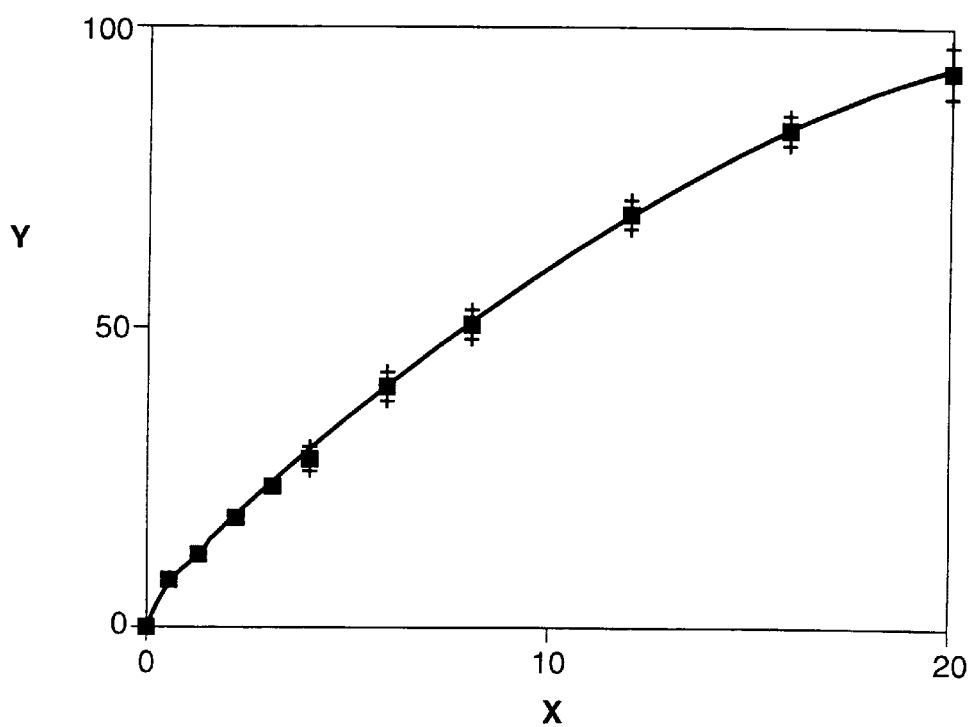
FIG. 4 is a graph showing pseudoephedrine release from vapor permeable membrane coated tablets.

Release-rate tests were conducted in simulated intestinal buffer at 37° C. with continuous stirring at 150 rpm. The simulated intestinal buffer solution is described in Example 7. Pseudoephedrine solubility is greater than 500 mg/ml in this buffer. The tablets were placed in 500 ml buffer. The tablets released pseudoephedrine steadily over a 20 hour period, releasing virtually all the pseudoephedrine contained in the tablets. FIG. 4 shows the release of pseudoephedrine from these tablets coated with VP membranes. In FIG. 4 percent pseudoephedrine release (Y) is graphed against time in hours (X).

EXAMPLE 9

Demonstration of Release of Glipizide from Vapor-permeable Membrane Coated Beads Beads containing 11.3 wt % glipizide, 82.7 wt % meglumine and 6% Klucel hydroxypropylcellulose were coated with a vapor-permeable membrane using the process described in Example 5. The coating solution was made from 3 wt % Kynar 711 polyvinylidene fluoride and 9.5 wt % deionized water dissolved in acetone.

Figure 5:
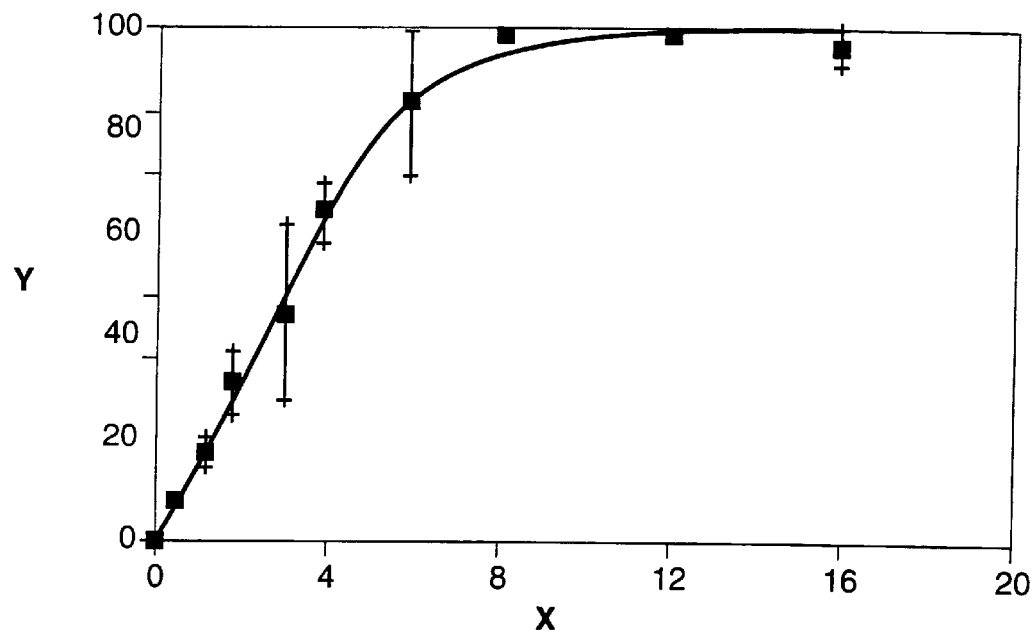
FIG. 5 is a graph showing glipizide release from vapor permeable membrane coated beads.

Release-rate tests were conducted in simulated intestinal buffer (described in Example 7) at 37° C. with continuous stirring. Glipizide solubility is about 0.34 mg/ml in this buffer. To determine drug release rate, approximately 500 mg of coated beads were placed in 0.5 liter simulated intestinal buffer for 20 hours. The VP coating allowed the drug to be released at a constant rate over an 8-hour period. The release-rate graph is shown in FIG. 5. In FIG. 5 percent glipizide release (Y) is graphed against time in hours (X).

EXAMPLE 10

Osmotic Release From Vapor-permeable Membrane Capsules

Vapor-permeable capsules were made in an analogous manner to that described in Example 1. The polymer solution used to make these capsules consisted of 17 wt % Kynar 460 polyvinylidene fluoride dissolved in propylenecarbonate at 120° C. In this case, the mandrels were placed in the hot polymer solution for 20 minutes before the mandrels were withdrawn slowly from the polymer solution. The coated mandrels were immediately quenched for 5 seconds in liquid nitrogen and then placed in an exchange bath of ethanol for 45 minutes. The capsules were allowed to dry, wetted with ethanol for removal from the mandrels and then cut for length.

The capsules were loaded with 2000 mg of powdered-drug mixture. The drug mixture consisted of 10 wt % glipizide and 90 wt % meglumine. The powder was loaded into the body of the capsule, then the cap of the capsule was placed on the body and a thin steam of sealing material was applied completely around the joint as described in Example 1. The sealant was allowed to air dry at room temperature before the capsules were tested.

The capsules were placed in solutions with different osmotic pressures. The receptor solutions (aqueous environment) were dextrose solutions of various concentrations with osmotic pressures of about 600, 1300, and 2800 KPa. The dextrose solutions were adjusted to a pH of 7.5 by adding sodium hydroxide. The glipizide and meglumine solution inside the capsules had an osmotic pressure of about 10,000 KPa.

Figure 6:
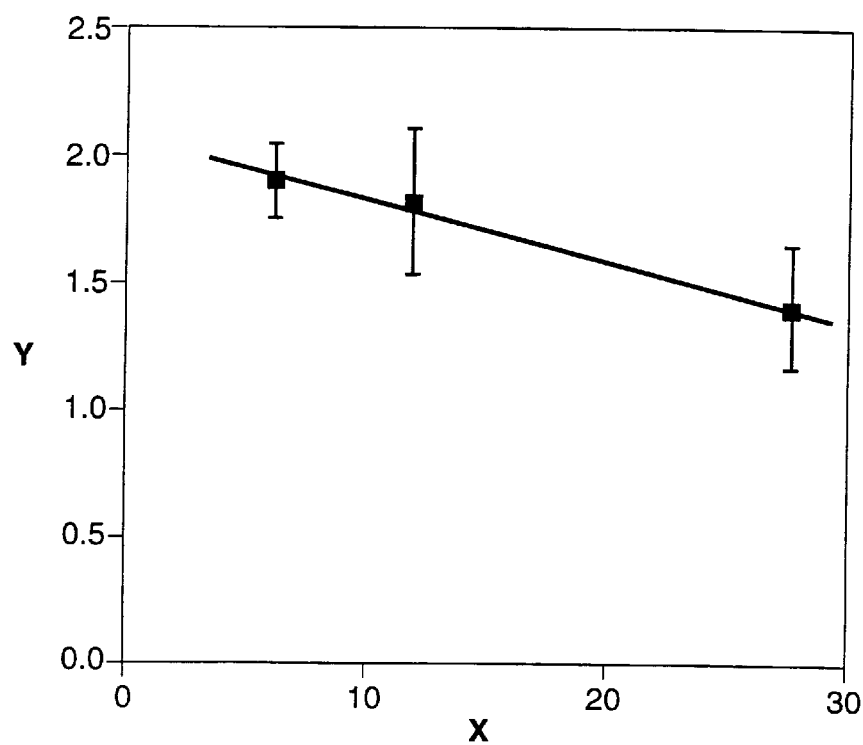
FIG. 6 is a graph showing osmotic release of glipizide from vapor-permeable membrane coated capsules into solutions that have different osmotic pressures.

The glipizide release rates from these capsules were higher in solutions having lower osmotic pressure, as shown in FIG. 6. In FIG. 6 glipizide release rate in mg/hour (Y) is graphed against osmotic pressure in atmospheres (X). The difference in osmotic pressure between the solution inside the capsule and the receptor solution outside the capsule is the osmotic driving force. Consequently, the osmotic release rates were proportional to the osmotic driving force. These data demonstrate that VP capsules can function as osmotic delivery systems for drugs.

EXAMPLE 11

Osmotic Release From Vapor-permeable Membrane Tablets

Pseudoephedrine tablets made by standard direct-compression techniques as described in Example 3 were precoated by spray-coating with a solution of 5 wt % sucrose and 5 wt % Methocel E6 Premium hydroxypropyl methylcellulose dissolved in deionized water using a STREA-1 (Aeromatic) spray-coater. The precoated tablets were then spray-coated using the STREA-1 with a solution consisting of 3 wt % Kynar 711 polyvinylidene fluoride, 15 wt % glacial acetic acid and 8 wt % water dissolved in acetone.

Release-rate tests were conducted in simulated intestinal buffer and in 20 wt % $CaCl_2$. The simulated intestinal buffer solution is described in Example 7. The osmotic pressure of the buffer is about 700 KPa and the osmotic pressure of 20 wt % $CaCl_2$ is about 25,000 KPa. The pseudoephedrine release rates from these tablets was higher in receptor solutions having lower osmotic pressure, as shown in FIG.

Figure 7:
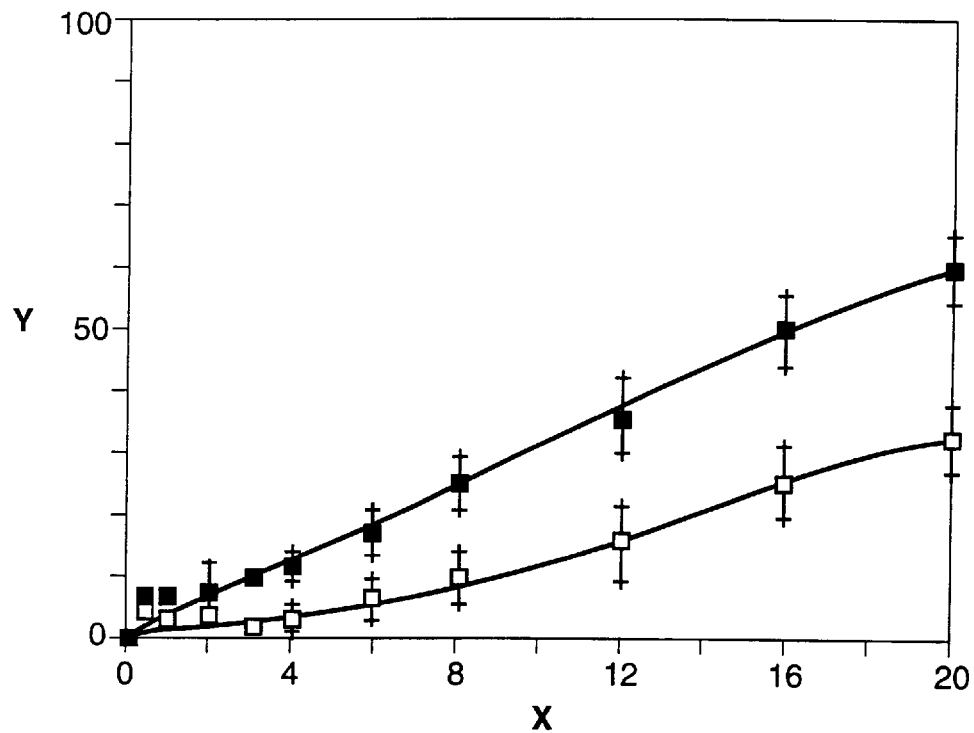
FIG. 7 is a graph showing the osmotic release of pseudoephedrine from vapor-permeable membrane coated tablets into solutions that have different osmotic pressures.

7. In FIG. 7 pseudoephedrine released as a percent of total pseudoephedrine (Y) is graphed against time in hours (X) for an intestinal buffer solution (denoted by a solid square) and a 20% CaCl$_2$ solution (denoted by an open square). The difference in osmotic pressure between the solution inside the tablet and the receptor solution outside the tablet is the osmotic driving force. Consequently, the osmotic release rates were proportional to the osmotic driving force.

EXAMPLE 12

Demonstration that Vapor-permeable Membrane Capsules are Very Effective at Limiting Ion Flux Vapor-permeable membrane capsules were made in the same manner as described in Example 7. The capsules were loaded with 200 mg of dextrose powder. The powder was loaded into the body of the capsule, the cap of the capsule was placed on the body and a thin steam of sealing material was applied completely around the joint as described in Example 1.

Figure 8:
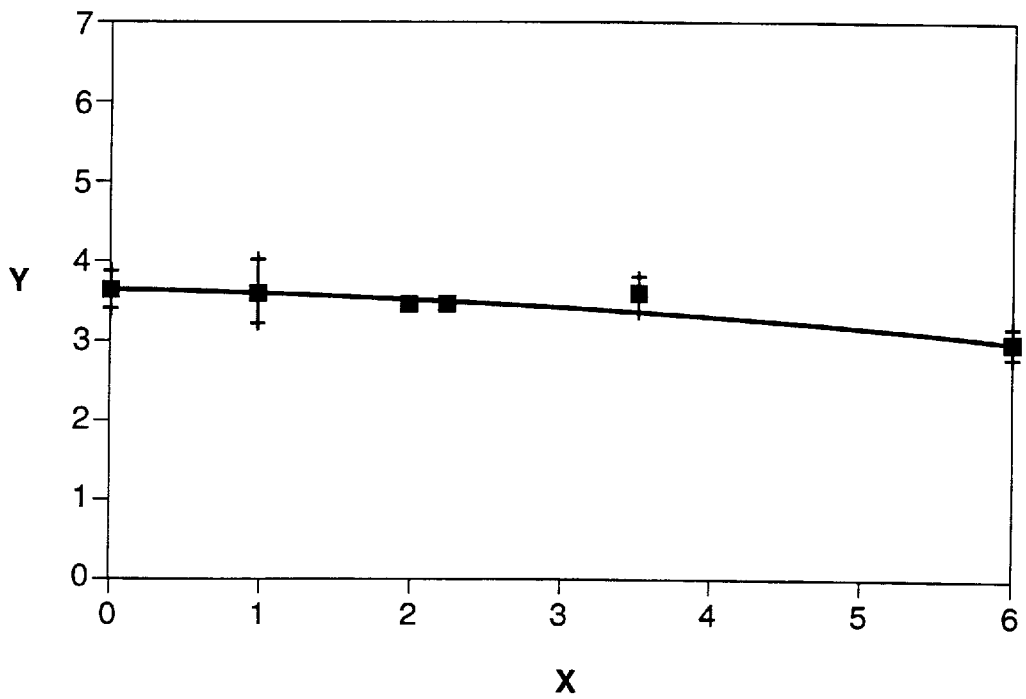
FIG. 8 is a graph showing the hydrogen ion flux into polyvinylidene fluoride vapor-permeable membrane coated capsules placed in gastric buffer, or distilled water.

The capsules were placed in deionized water and in simulated gastric buffer (pH 1.2, containing sodium chloride and hydrochloric acid with an osmotic pressure of 700 KPa) and the pH of the core was monitored to determine the effect of the receptor solution. A portion of the capsules were placed in 1 liter of simulated gastric buffer at 37° C. with continuous stirring. After the desired exposure time in gastric buffer the capsules were removed, rinsed, blotted, cut open and 10 ml of deionized water was added. The pH of the resulting solution indicated the hydrogen ion concentration inside the capsule core. The pH of the core solution was recorded and graphed. The pH did not change with time which indicates virtually no hydrogen ions were getting into the capsule core. As a control, capsules from the same batch were placed in deionized water and the pH of the core monitored as described above. The results are shown in FIG. 8. In FIG. 8 the pH inside the capsules (Y) is graphed against time in hours (X) for a gastric buffer solution (denoted by a solid triangle) and a distilled water solution (denoted by a solid square). The core pH is the same regardless of the pH of the receptor solution. Therefore no ions were transported through the VP capsule wall, only water vapor.

EXAMPLE 13

Demonstration That Vapor-permeable Membrane Coating on Beads Allow Vapor Transport While Limiting Ion Flux Dowex MSC-1 ion-exchange resin beads were coated with a VP membrane coating as described in Example 6.

The beads were leak tested by placing 500 mg of beads in a 100 ml 0.5M sodium chloride solution and monitoring the pH of the solution. If any leaks were present that allowed an influx of liquid water into the beads, then the sodium ions would also enter the beads and exchange with the hydrogen ions on the resin inside the beads. The hydrogen ions would exit the beads causing an obvious drop in the pH of the receptor solution.

Leak-free beads (i.e., coated beads that did not allow this sodium-hydrogen ion exchange, exhibited by no change in pH in the sodium chloride solution for 20 hours) were then tested for vapor transport with an ammonia absorption test. The beads were prewet and placed in sealed containers containing a buffer solution consisting of 10.0 mM ammonium chloride adjusted to pH 11 with sodium hydroxide. The ammonia concentration in the buffer was determined and recorded with time. Over a four-hour period the ammonia concentration in the buffer solution was reduced by over an order in magnitude, indicating the bead coatings were permeable to ammonia vapor. This example demonstrates that the VP membrane coatings on beads allow vapor transport while preventing ion transfer.

EXAMPLE 14

Demonstration That Release Rate can be Controlled by Surface Tension in the Core Vapor-permeable membrane capsules were made in the same manner as described in Example 1.

The capsules were loaded with three different powdered-drug mixtures having different surface tensions. The first set of capsules contained 200 mg of a drug mixture consisting of 10 wt % glipizide and 90 wt % meglumine. The approximate surface tension of this mixture in solution was 68 dyn/cm. The second set of capsules contained a drug mixture consisting of 8 wt % glipizide, 42 wt % meglumine and 50 wt % polyethylene glycol and in solution had an approximate surface tension of 48 dyn/cm. The third type capsule contained 200 mg of a drug mixture consisting of 10 wt % glipizide, 75 wt % meglumine, and 15 wt % sodium lauryl sulfate and in solution had an approximately surface tension of 35 dyn/cm.

Figure 9:
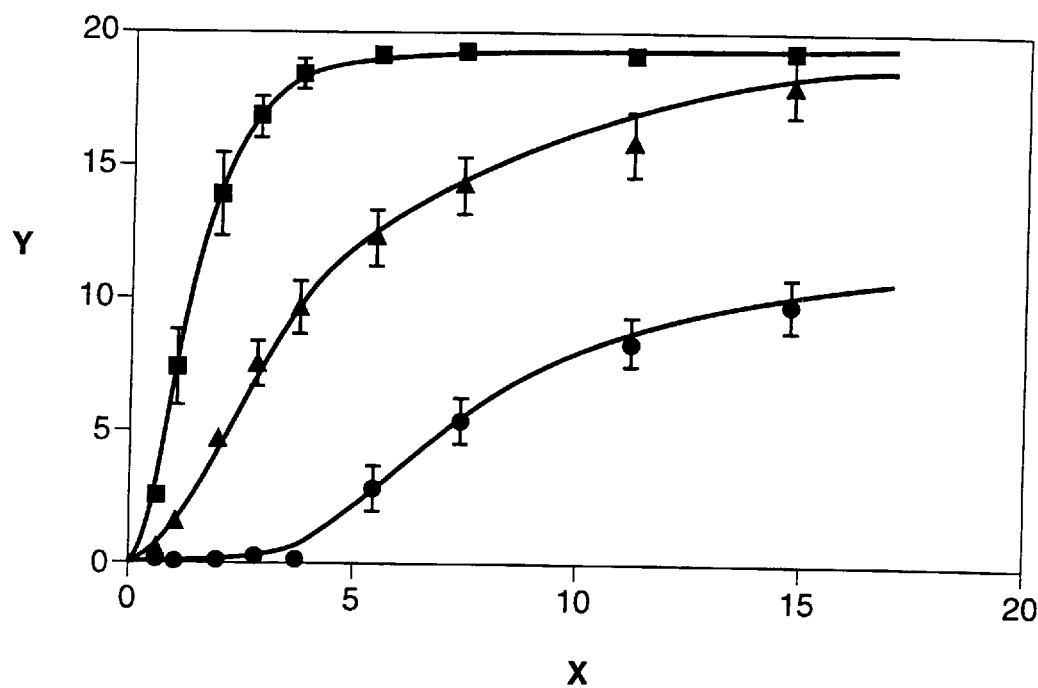
FIG. 9 is a graph of the release rate of glipizide from polyethylene vapor-permeable membrane coated capsules showing that the release rate can be controlled by the surface tension in the capsule core.

Release-rate tests were conducted as described in Example 7. The release rate of glipizide from the VP capsules increased with decreasing surface tension of capsule excipients as shown in FIG. 9. In FIG. 9 glipizide in mg released (Y) is graphed against time in hours (X) for the three different core excipient mixtures described above: meglumine (denoted by a solid circle); meglumine/polyethylene glycol (denoted by a solid triangle); and meglumine/sodium lauryl sulfate (denoted by a solid square).

We claim:

1. An osmotic device for the controlled release of a beneficial agent to an aqueous environment comprising:
   a. a hydrophilic formulation comprising a beneficial agent, a surfactant and an osmagent;
   b. a wall surrounding said hydrophilic formulation, said wall formed at least in part of a semipermeable hydrophobic membrane having pores that have an average pore size between about 0.1 $\mu$m and 30 $\mu$m, said pores substantially filled with a gas phase, said hydrophobic membrane permeable to water in the vapor phase and said hydrophobic membrane impermeable to liquid water at a pressure less than 100 Pa, wherein said device does not release the beneficial agent through an orifice but delivers the beneficial agent through the hydrophobic membrane pores as they become wetted.

2. The osmotic device as recited in claim 1 wherein the release of beneficial agent is substantially by osmotic pumping.

3. The osmotic device as recited in claim 2 wherein the semipermeable hydrophobic membrane has a water vapor transmission rate greater than 2 g-mm/m$^2$-24 hours, a water contact angle greater than 50 degrees, a void volume of between 5% and 95% and a thickness of about 5 $\mu$m to 5 mm, and wherein the semipermeable hydrophobic membrane in the nonporous state is substantially impermeable to the beneficial agent and has an intrinsic permeability to water of less than $1 \times 10^{-6}$ cc (STP)-cm/cm$^2$-sec-cmHg.

4. The osmotic device as recited in claim 3 wherein the hydrophilic formulation includes an aqueous swellable material.

5. The osmotic device as recited in claim 4 wherein said semipermeable hydrophobic membrane material is polyethylene, polyvinylidene fluoride, polyacrylic acid derivatives, cellulose esters, cellulose ethers, natural waxes or synthetic waxes.

6. The osmotic device as recited in claim 5 wherein said membrane material is polyethylene or polyvinylidene fluoride.

7. The osmotic device as recited in claim 6 wherein said membrane material is polyvinylidene fluoride.

8. The osmotic device as recited in claim 7 wherein the osmagent is a sugar.

9. The osmotic device as recited in claim 8 wherein the hydrophilic formulation has a surface tension of about 60–75 dyn/cm.

10. The osmotic device as recited in claim 9 wherein the hydrophilic formulation includes polyethylene glycol and the hydrophilic formulation has a surface tension of about 40–60 dyn/cm.

11. The osmotic device as recited in claim 10 wherein the hydrophilic formulation includes sodium lauryl sulfate and the hydrophilic formulation has a surface tension of about 25–40 dyn/cm.

12. The osmotic device as recited in claim 1 wherein the release of beneficial agent is substantially by osmotic bursting.

13. The osmotic device as recited in claim 12 wherein the semipermeable hydrophobic membrane has a water vapor transmission rate greater than 2 g-mm/m$^2$-24 hours, a water contact angle greater than 50 degrees, a void volume of between 5% and 95% and a thickness of about 5 μm to 5 mm, and wherein the semipermeable hydrophobic membrane in the nonporous state is substantially impermeable to the beneficial agent and has an intrinsic permeability water of less than $1 \times 10^{-6}$ cc (STP)-cm/cm$^2$-sec-cmHg.

14. The osmotic device as recited in claim 13 wherein the hydrophilic formulation includes an aqueous swellable material.

15. The osmotic device as recited in claim 14 wherein said semipermeable hydrophobic membrane material is polyethylene, polyvinylidene fluoride, polyacrylic acid derivatives, cellulose esters, cellulose ethers, natural waxes or synthetic waxes.

16. The osmotic device as recited in claim 15 wherein said membrane material is polyethylene or polyvinylidene fluoride.

17. The osmotic device as recited in claim 16 wherein said membrane material is polyvinylidene fluoride.

18. The osmotic device as recited in claim 17 wherein the osmagent is a sugar.

19. The osmotic device as recited in claim 18 wherein the hydrophilic formulation has a surface tension of about 60–75 dyn/cm.

20. The osmotic device as recited in claim 18 wherein the hydrophilic formulation includes polyethylene glycol and the hydrophilic formulation has a surface tension of about 40–60 dyn/cm.

21. The osmotic device as recited in claim 18 wherein the hydrophilic formulation includes sodium lauryl sulfate and the hydrophilic formulation has a surface tension of about 25–40 dyn/cm.

22. The osmotic device as recited in claim 1 wherein the beneficial agent is a pharmaceutical or veterinary agent.

23. The osmotic device as recited in claim 22 wherein the device is a capsule.

24. The osmotic device as recited in claim 22 wherein the device is a tablet.

25. The osmotic device as recited in claim 22 wherein the device is a bead.

26. A method for the controlled delivery of a beneficial agent to an aqueous environment of use which comprises placing the device of claim 1 into the aqueous environment of use.

27. An osmotic device for the controlled release of a beneficial agent to an aqueous environment comprising:
   a. a hydrophilic formulation comprising a beneficial agent that is also an osmagent and a surfactant;
   b. a wall surrounding said hydrophilic formulation, said wall formed at least in part of a semipermeable hydrophobic membrane having pores that have an average pore size between about 0.1 μm and 30 μm, said pores substantially full of a gas phase, said hydrophobic membrane permeable to liquid water in the vapor phase and said hydrophobic membrane impermeable to water at a pressure less than 100 Pa, wherein said device does not release the beneficial agent through an orifice but delivers the beneficial agent through the hydrophobic membrane pores as they become wetted.

28. A method for the controlled delivery of a beneficial agent to an aqueous environment of use which comprises placing the device of claim 27 into the aqueous environment of use.

* * * * *